(12) United States Patent
Kwun et al.

(10) Patent No.: US 6,968,727 B2
(45) Date of Patent: Nov. 29, 2005

(54) CALIBRATION METHOD AND DEVICE FOR LONG RANGE GUIDED WAVE INSPECTION OF PIPING

(75) Inventors: Hegeon Kwun, San Antonio, TX (US); Sang-Young Kim, San Antonio, TX (US); Glenn M. Light, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 361 days.

(21) Appl. No.: 10/425,528

(22) Filed: Apr. 29, 2003

(65) Prior Publication Data

US 2004/0216512 A1    Nov. 4, 2004

(51) Int. Cl.$^7$ ............................................. G01N 29/04
(52) U.S. Cl. ........................................ 73/1.82; 73/1.86
(58) Field of Search ................................ 73/1.79, 1.81, 73/1.82, 1.86, 598, 600

(56) References Cited

U.S. PATENT DOCUMENTS

| | | | |
|---|---|---|---|
| 4,270,389 A * | 6/1981 | Shiraiwa et al. | 73/612 |
| 4,393,711 A * | 7/1983 | Lapides | 73/592 |
| 4,522,064 A * | 6/1985 | McMillan | 73/592 |
| 4,545,251 A * | 10/1985 | Uchida et al. | 73/631 |
| 4,660,419 A * | 4/1987 | Derkacs et al. | 73/622 |

* cited by examiner

*Primary Examiner*—Robert Raevis
(74) *Attorney, Agent, or Firm*—Gunn & Lee, P.C.

(57) ABSTRACT

The present invention is for a simple, reliable and inexpensive method to calibrate a defect signal to determine the size of a defect in a pipe. A first reflected signal is received from the test area of the pipe. After attaching a clamp, a second reflected signal is received from the test area of the pipe. If defects are in the test area, by appropriate calculations using the first reflected signal and the second reflected signal, the size of the defect can be determined.

4 Claims, 4 Drawing Sheets

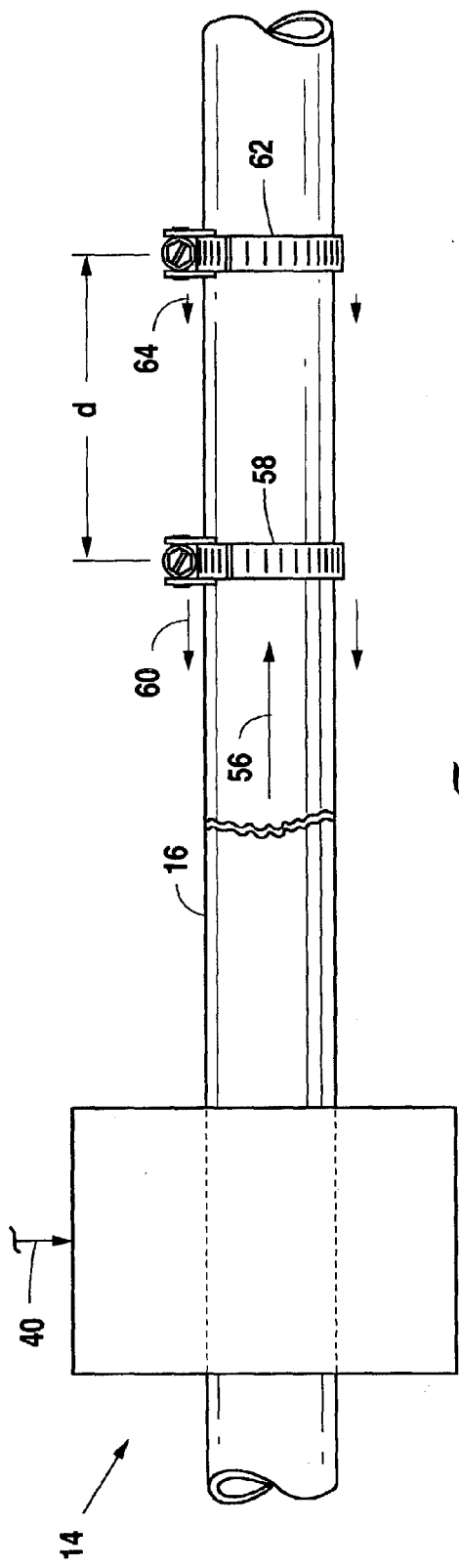
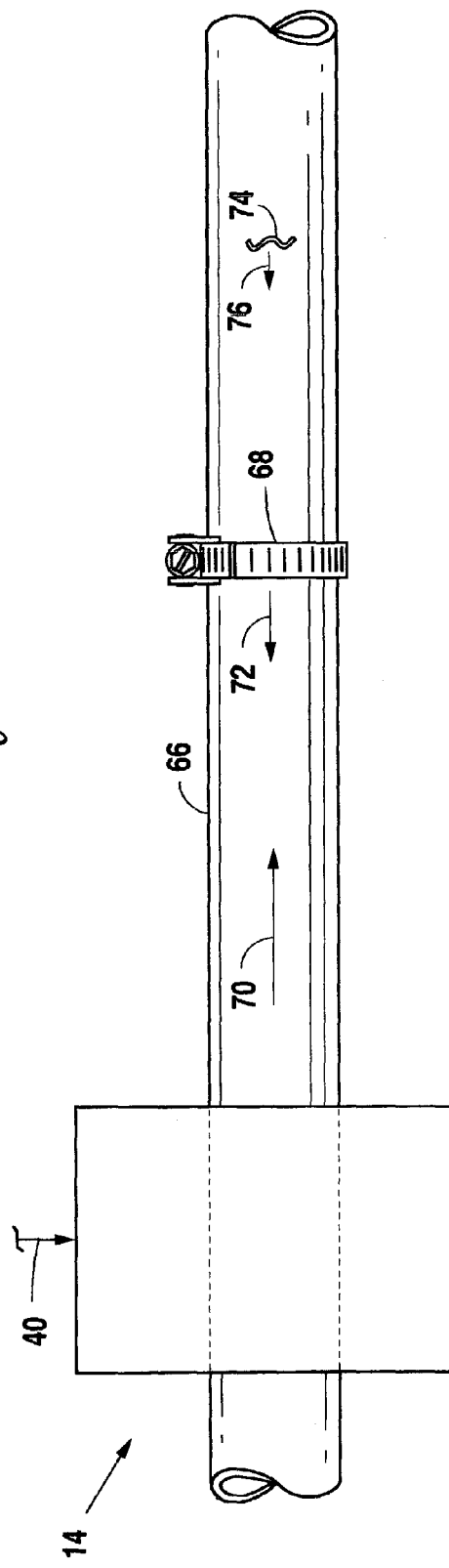

CALIBRATION METHOD AND DEVICE FOR LONG RANGE GUIDED WAVE INSPECTION OF PIPING

BACKGROUND OF THE INVENTION

1. Field of the Invention

The present invention relates generally to a method of calibration and more particularly to a calibration method and device for use in long range guided wave inspection of piping.

2. Description of the Prior Art

The use of long range guided wave techniques for inspection of large areas of structures, including piping, from a single sensor location is an emerging technology. For piping, the technique involves the launching of a pulse of guided waves along the length of the pipe. Any reflected signals are detected by a receiver. Reflected signals may be from (a) the natural structure of the pipe or (b) corrosion or cracks in the pipe.

The occurrence time of the reflected signal from the time of launch until received can be used to determine the axial location of the defect. The amplitude of the reflected signal will determine the severity of the defect.

The long range guided wave technique gives a one hundred percent volumetric inspection of a long length of piping from a single probe location. In a typical inspection over a hundred feet of pipe can be inspected at frequencies of approximately 100 kHz or less for pipes that are not coated or buried. This long range guided wave inspection technique is particularly useful for remote inspection of difficult to access areas by launching and receiving reflected waves from an accessible location. For example, the guided waves can travel along the pipe under installation or at high elevations that are inaccessible.

The use of long range guided wave techniques for comprehensive inspection of piping is gaining rapid acceptance as a cost effective inspection method in various industries, including gas, oil, petrochemical, and electric power. This is particularly true where piping is a primary component of the facility. One reason why the long range guided wave technique is gaining popularity is because of its minimum preparation and inspection time.

The magnetostrictive (MsS) sensor technology for guided waves has been extensively developed and patented by Southwest Research Institute. In the magnetostrictive techniques, Southwest Research Institute is one of the world leaders in using this technology for long range guided wave inspection. Just some of the patents owned by Southwest Research Institute in this area include U.S. Pat. Nos. 5,456,113; 5,457,994; 5,581,037; 5,767,766; 6,212,944; 6,294,912; and 6,429,650.

While Southwest Research Institutes owns other patents utilizing the magnetostrictive technology, it is believed these provide a good illustration of the prior magnetostrictive patents that exist.

For the benefit of those who do not understand the magnetostrictive effect, the magnetostrictive effect refers to a physical dimension change in ferromagnetic materials that occurs when a magnetic field is applied to the material. Mechanical waves are generated by introducing a pulse current into a transmitting coil adjacent to a ferromagnetic material that, in turn, changes the magnetization within the material located near the transmitting coil. The change in magnetization within the material located near the transmitting coil causes the material to change its length locally in a direction parallel to the applied field. This abrupt local dimension change, caused by the magnetostrictive effect, generates a mechanical wave (called a guided wave) that travels through the ferromagnetic material at a fixed speed.

When a mechanical wave is reflected back, it indicates a physical barrier, such as (a) end of the ferromagnetic material, (b) defect in the ferromagnetic material, or (c) some other geometric changes, such as welds. When the reflected mechanical wave (guided wave) reaches a detection coil, the mechanical wave causes a changing magnetic flux in the detection coil through the inverse magnetostrictive effect. This changing magnetic flux induces an electric voltage within the detection coil that is proportional to the magnitude of the reflected mechanical wave. The transmitting coil and the detecting coil can be (a) the same coil or (b) separate but identical coils.

Despite all the advances that have been made in magnetostrictive techniques, there still needs to be a simple and accurate way to calibrate the magnetostrictive inspection system. Calibration is necessary to quantify the reflected signals and relate the reflected signals to the size of a defect. Calibration is necessary to determine the scale of the reflected signal in relation to a percentage defect. In conventional inspection techniques, such as ultrasonic or eddy current, calibration may be achieved by using reflected signals from a reference reflector. The reference reflector may be the back wall, a side drilled hole, a flat bottom hole or a fixed diameter reference block. By using a known type of reflector, calibration of the scale can occur. Also another manner of calibration is by using a short piece of reference pipe with reference reflectors. However, the reference pipe has to match the pipe under test. That is not possible most of the time.

The size (and hence scale) of the reflected signal will vary according to the pipe itself. The thickness or diameter of the pipe, the physical condition of the pipe (new, rusty, etc.), as well as the material out of which the pipe is made affects the transmission of a magnetostrictive signal therethrough. Therefore, a reference signal that is used in one size pipe made of a particular material does not apply to a different size pipe made from another material, both of which may be ferromagnetic.

Also the coupling between the guided wave probe in the pipe is variable from one situation to the next with the variations being considerable in the field from pipe to pipe and from location to location. Variations can depend upon the diameter of the pipe, wall thickness of the pipe, and condition of the pipe under inspection. Calibration of the scale by using a reference pipe has been found to be impractical in most occasions. Therefore, the present invention is directed toward calibrating the scale of the reflected signal in relation to percentage defect by using guided wave signals in the pipe that is under inspection.

One method of calibration of the scale that has been used in the past is simultaneously detecting the transmitted signal and the reflected signal by using a second guided wave probe installed some distance away and using the transmitted signal as the reference. While this approach provides for fairly good calibration, it is not always practical because of the increased inspection time and distance at which the second probe must be located.

As a compromise solution, signals from girth welds in pipe have generally been used as a calibration reference. This approach, though convenient, is not reliable. The welds are not identical and their signals vary widely from pipe to pipe and from location to location. Even the skills of the welder in creating the girth weld can greatly affect the reflected signal.

All of these problems led to the need for a direct method to calibrate the scale that is simple, reliable and inexpensive for long range guided wave inspection of pipes.

This invention is needed to enhance the reliability of the results received from long range guided wave inspection of piping.

SUMMARY OF THE INVENTION

It is therefore an object of this invention to provide a simple, reliable and inexpensive method and device for directly calibrating the scale of guided wave signals in the pipe under inspection.

It is another object of this invention that the simple, reliable and inexpensive method and device for calibrating the scale of guided wave signals that can also be used in other cylindrical structures, such as tubing, rods or cables.

It is a further object of the present invention to use a clamp around the pipe under inspection to give a reflected signal that can be used as a reference signal for a certain percentage defect.

It is yet another object of this invention to use the reflected signal from the clamp and compare it to a defect signal to determine the size of the defect.

It is yet another object of the present invention to use reflected signals from at least two clamps spaced apart a known distance and compare the reflected signals to determine attenuation that occurs in the pipe. By knowing the attenuation that occurs over a linear distance, the size of the defect from a defect signal can then be calculated.

In the present invention, a guided wave is induced into a pipe by a guided wave probe and travels along the pipe. Prior to introducing the guided wave into the pipe, a clamp is securely tightened on the pipe at some distance away from the dead zone of the guided wave probe. The clamp causes a reflected signal to be reflected back to the guided wave probe. The reflected signal from the clamp (from now on "clamp signal") is then used as a calibration reference. By comparing magnitudes of other reflected signals to the clamp signal, the magnitude of the defect can be determined. The time of travel of the reflected signal from launch until received back at the probe can be used to determine the location of a potential defect.

To determine the amount of attenuation, two clamps may be attached to the pipe a known distance apart. By knowing the distance between the clamps, the amount of attenuation per linear distance can be determined. By knowing the amount of attenuation over a linear distance, the size of the defect based upon amplitude of the reflected signal can be more accurately determined.

By using the present invention, the scale of the defect signals as a percentage defect can be more reliably determined in the field on the pipe that is under test.

BRIEF DESCRIPTION OF THE DRAWINGS

FIG. 3 is a partial schematic view illustrating the use of two clamps to determine attenuation of guided wave signals over a distance d.

FIG. 4 is a partial schematic block diagram illustrating the use of a clamp for calibration and determining the size of defects in a pipe.

DETAILED DESCRIPTION OF THE PREFERRED EMBODIMENT

Figure 1:
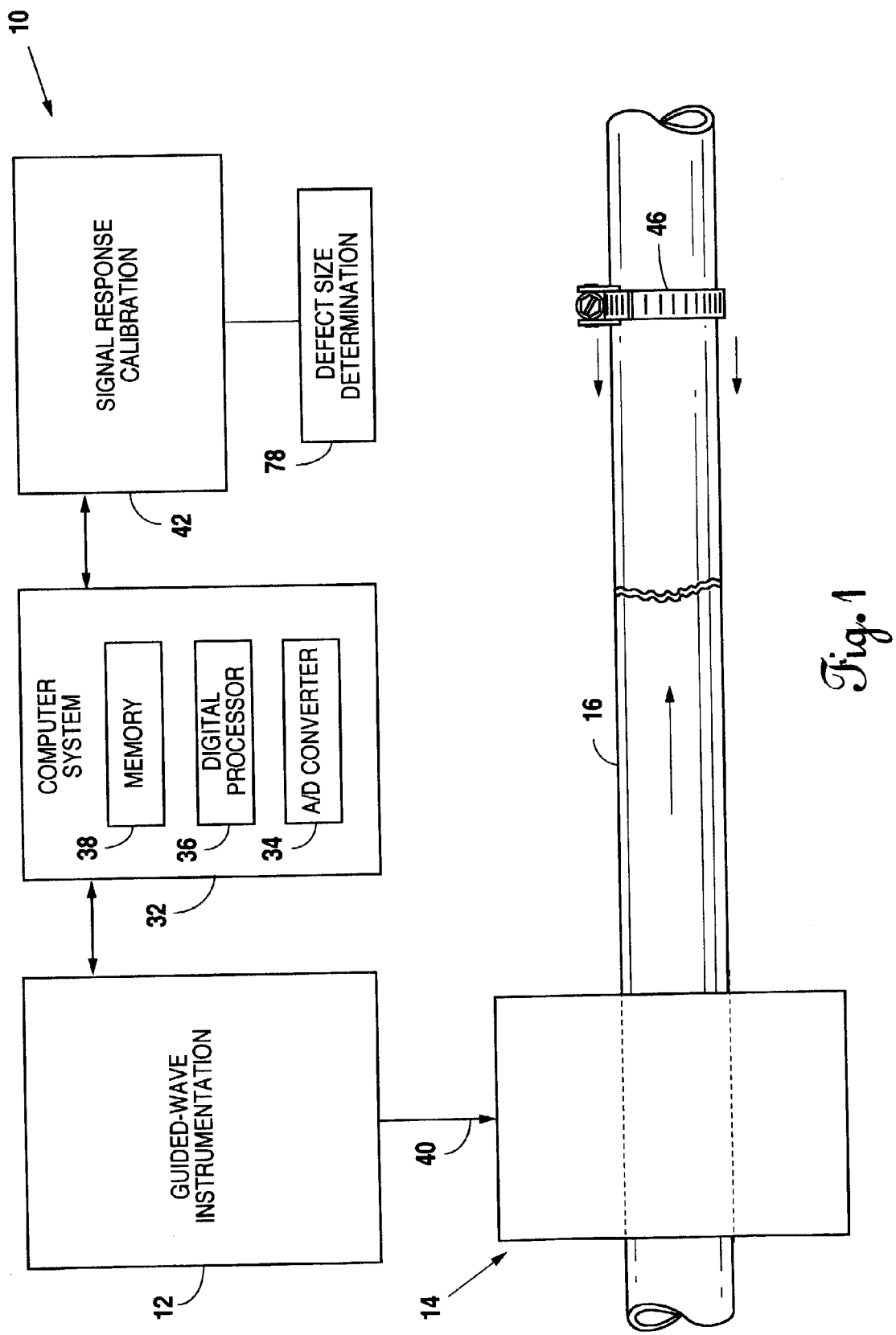
FIG. 1 is a schematic block diagram showing the preferred embodiment of the present invention.

The present invention is directed towards a simple, reliable, inexpensive method of direct calibration in the field of the scale of a reflected guided wave using guided wave techniques. The scale then can be used to determine the percentage defect represented by any unknown reflected signal. Reference is made to FIG. 1 for description of a complete system that could be used with the present invention. In FIG. 1, an inspection system 10 is shown that includes a guided-wave instrumentation 12 with associated transmitter/receiver probe 14. The transmitter/receiver probe 14 encircles a pipe 16 under test.

The guided-wave instrumentation 12 generates the appropriate signal for delivery to the transmitter/receiver probe 14 through connecting cable 40. A guided wave is then generated in the pipe 16 and transmitted along the length of the pipe 16.

The transmitter/receiver probe 14 acts not only as a transmitter, but also as a receiver of any reflected signals. Any signals reflected back along pipe 16 are detected by the transmitter/receiver probe 14 and are amplified and filtered by the guided-wave instrumentation 12, which amplified/filtered signal is fed to a computer system 32. Inside of the computer system 32 is contained an A/D converter 34, digital processor 36, and memory 38, which work together to receive, digitize and analyze the signal received from the transmitter/receiver probe 14.

Typically the transmitted signal from the guided-wave instrumentation 12 is less than 100 kHz. The frequencies of the signals used may vary depending upon the pipe being tested and its environment.

In the present long-range guided-wave inspection techniques, there have been problems in the past with calibration of the detected signals. Calibration of the detected signals is needed so that defect signal received can be equated to a certain percentage defect.

The present invention has a signal response calibration 42 that is used to calibrate the clamp signal. The signal response calibration 42 may be a part of the software of computer system 32.

The amplitude, $A_i$, of a signal reflected from a geometric feature in the pipe 16 under inspection can be expressed as $$A_i = A_0 R_i e^{-2\alpha X_i} \qquad \text{Eq.(1)}$$

where $A_0$ is the amplitude of the transmitted signal from the transmitter/receiver probe 14, $R_i$ is the reflection coefficient of the geometric feature i (such as weld or defect and i=1, 2, 3, etc.) from which the signal $A_i$ was reflected, $\alpha$ is the attenuation coefficient of the wave in the pipe 16 under test, and $X_i$ is the distance from the guided-wave probe to the geometric feature i. See FIG. 5. Except for $A_i$, which can be measured from the detected data, all other parameters are unknown at this point.

When guided-wave data are taken again after installing clamp 46 on the pipe 16 at a location X, when $X<X_i$, the signal from the geometric feature i is somewhat reduced from the previous amplitude detected before installing the clamp 46. This reduction in amplitude occurs because the transmitted signal loses some of its energy when it is partially reflected by the clamp 46. The amplitude of the clamp signal, $A_c$, and the amplitude of the geometric feature signal obtained with the clamp 46 on the pipe 16, $A_{ic}$, can be expressed as:

$$A_c = A_0 R_c e^{-2\alpha X} \qquad \text{Eq.(2)}$$

$$A_{ic} = A_0(1-R_c^2) R_i e^{-2\alpha Xi} \qquad \text{Eq.(3)}$$

where $R_c$ is the reflection coeffeicient of the clamp 46.

Then, utilizing Equations (1) and (3) and the amplitudes of $A_i$ and $A_{ic}$, measured from the data taken without and with the clamp 46, the reflection coefficient of the clamp, $R_c$ is determined as:

$$R_c^2 = 1 - (A_{ic}/A_i) \qquad \text{Eq.(4)}$$

This process of determining $R_c$ is the same as the process of calibrating the clamp signal.

Using the value of $R_c$ determined per Equation (4) as the calibration reference, the reflection coefficient, $R_j$, of any geometric feature j detected in the data (either welds or defects) are determined approximately as follows:

$$R_j = R_c (A_j/A_c) e^{-2\alpha(X-Xj)} = (R_c/(1-R_c^2))(A_{jc}/A_c) e^{-2\alpha(X-Xj)} \qquad \text{Eq.(5)}$$

where $A_j$ and $A_{jc}$ are the signal amplitude of the geometric feature j located at distance $X_j$ from the transmitter/receiver probe 14. The value of $R_j$ is directly proportional to the defect size and, thus, the defect size is determined from the value of $R_j$. To calculate $R_j$ per Equation (5), the attenuation value $\alpha$ is needed. There are three ways to treat $\alpha$ in ascending order of accuracy: (a) ignore $\alpha$ by assuming $\alpha=0$, (b) determine the value from the decay pattern of weld signals, and (c) determine the value by using two clamp signals (see FIGS. 3 and 4).

The calibration process involves the following steps:

(1) Acquire two sets of data; one without a clamp and the other with a clamp.

(2) Among the signals that occurred after the clamp signal location in the data, select a signal whose amplitude was the largest.

(3) Using amplitudes of the selected signal in both sets of data, calculate $R_c$ per Equation (4).

The accuracy of the above calibration can be improved by repeating the above process using the amplitudes of the additional signals in the data (namely, using the second largest signal, third largest signal, and so forth) and then averaging the values of $R_c$ thus calculated.

Figure 5:
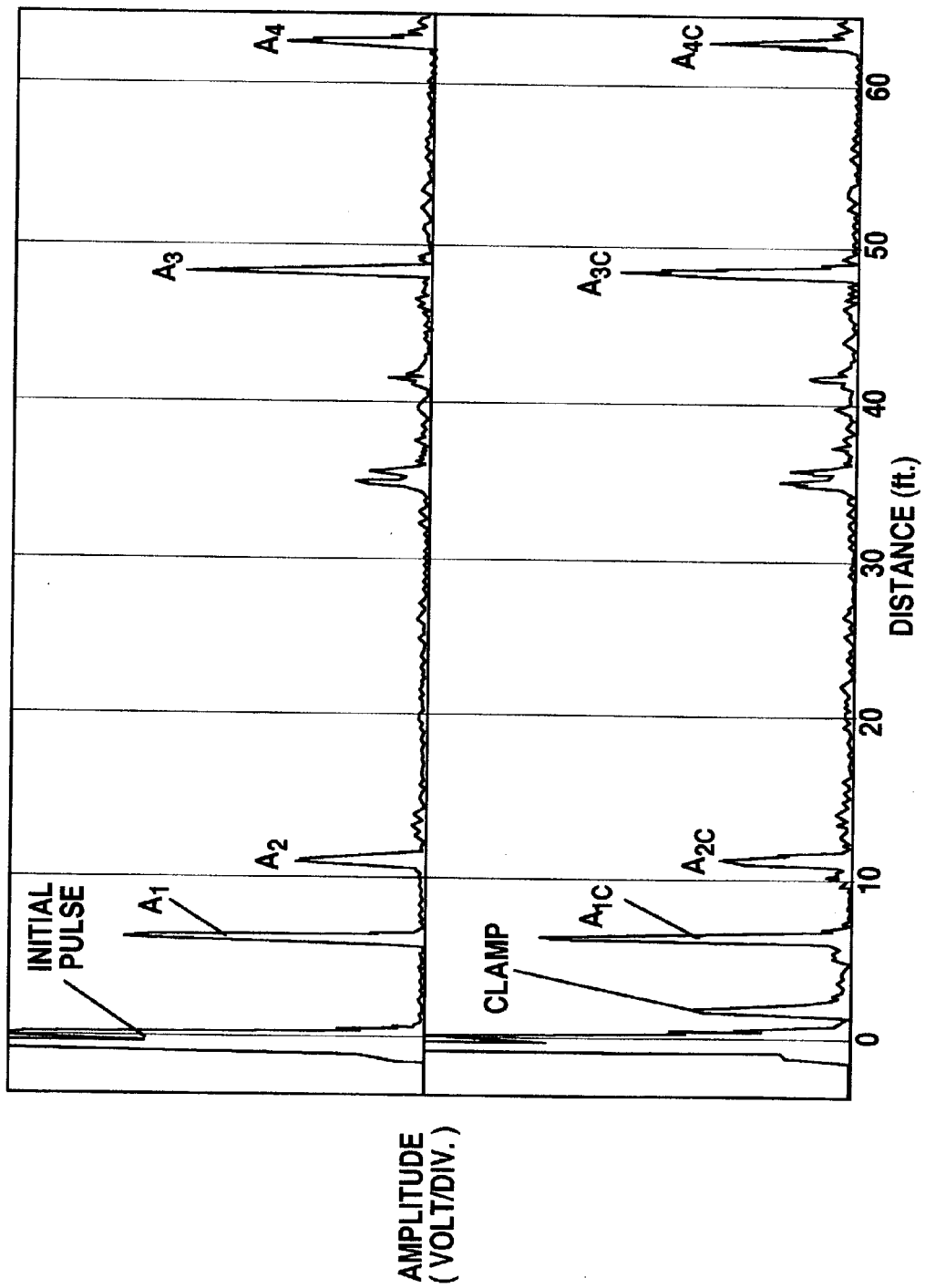
FIG. 5 is two sets of data obtained for calibration, with and without a clamp.

To illustrate the above calibration process, an example of the two sets of data that were obtained with (bottom) and without (top) a clamp is given in FIG. 5. The data were obtained from a 6-⅝-inch-OD, 0.28-inch-wall pipeline using 32-kHz torsional guided waves. The amplitude of the signals $A_1$ through $A_4$ indicated in the top trace of FIG. 5 became somewhat smaller when the clamp was installed on the pipe; for example $A_3=0.5709$ volts and $A_{3c}=0.5639$ volts. Utilizing Equation (4) and the amplitudes of $A_3$ and $A_{3c}$, the reflection coefficient of the clamp is calculated to be $R_c=0.11$. Then, using the amplitude of the clamp signal, $A_c=0.3787$ volts, and Equation (5) with $\alpha=0$, the reflection coefficients of the geometric features 1 through 4 are calculated to be $R_1=0.21$, $R_2=0.09$, $R_3=0.17$, and $R_4=0.11$. These reflection coefficient values are then correlated to defect size.

Figure 2C:
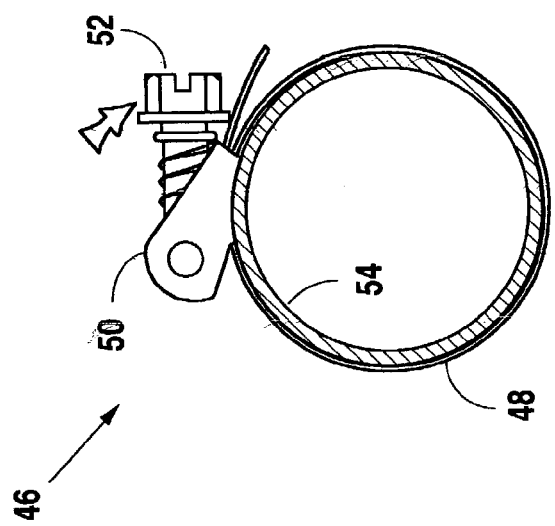
FIGS. 2A, B and C are side elevational views of a clamp being tightened on a pipe for use in calibration.
Figure 2B:
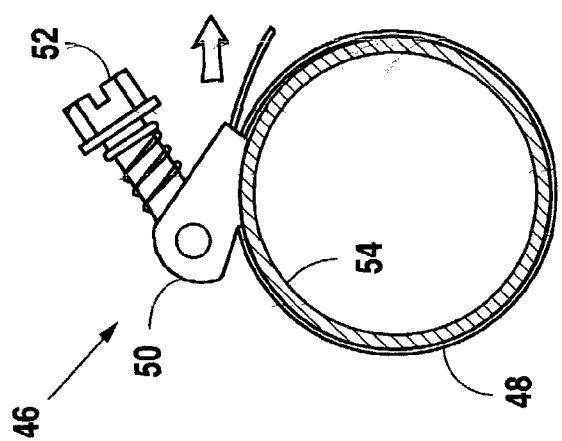
Figure 2A:
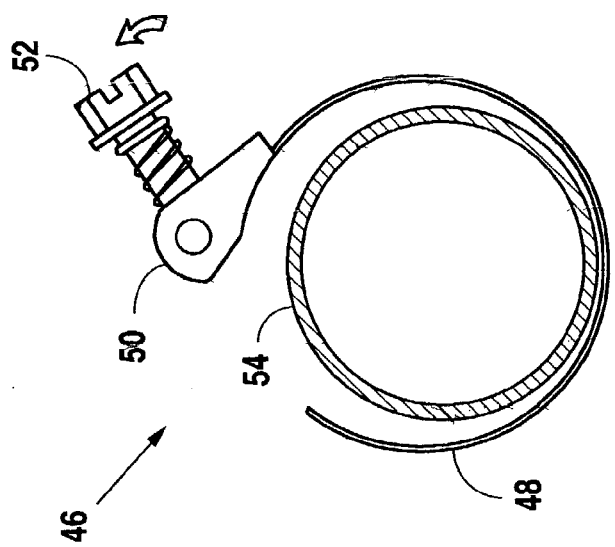

Referring to FIGS. 2A, B, and C in combination, a further description of the clamp 46 is given. The clamp 46 consists of a band 48 connected on one end to screw clamp 50 that may be tightened by screw 52. The band 48 of the clamp 46 is looped around a standard pipe 54 as shown in FIG. 2A. The unconnected end of the band 48 is extended through the screw clamp 50 and tightened by screw 52 as shown in FIG. 2B. The screw 52 is tightened to a predetermined level of torque and thereafter screw 52 is rotated over a breakover point (not shown) as is illustrated in FIG. 2C. By using a specified level of torque, variations in signal amplitude reflected by the clamp 46 can be kept to a minimum. Different types of clamps 46 can be used, such as a commercial stainless steel snap lock/quick release clamps manufactured by Ideal and sold under the Tridon brand, or the stainless steel clamps manufactured by Breeze Industrial Products Corp.

While encircling clamp 46 is shown on pipe 54, other types of clamp and device (such as U-bolts) that can reflect guided waves can be used on pipe 54.

By use of the clamp as illustrated in FIGS. 2A, B, and C, in the system as pictorially shown in FIG. 1, the invention will be further described. The guided-wave instrumentation 12 will generate a pulse signal that will be transmitted through connecting cable 40 to the transmitter/receiver probe 14 and propagate down the pipe 16. At the clamp 46, a portion of the wave propagating down the pipe 16 will be reflected back toward the transmitter/receiver probe 14. As illustrated by the size of the arrows, only a portion of the transmitted signal will be reflected back as a reflected signal to the transmitter/receiver probe 14. The reflected signal is detected by the by the transmitter/receiver probe 14, which reflected signal is amplified and filtered as the reflected signal is defected by the guided-wave instrumentation 12.

Referring now to FIG. 4, a pipe 66 is shown under test. The same type of transmitter/receiver probe 14 as shown in FIG. 1 is utilized, as well as the same type of guided-wave instrumentation 12, computer system 32, signal response calibration 42, data comparison 46, and defect size determination 78 as illustrated in FIG. 1.

The pipe 66, which is under test, has a clamp 68 attached thereto, which clamp 68 is similar to those described in conjunction with FIG. 2. A transmitted signal 70 moves down the pipe 66 toward clamp 68. At clamp 68, a first reflected signal 72 is reflected back towards transmitter/receiver probe 14. By knowing the distance between clamp 68 and transmitter/receiver probe 14, the size of the transmitted signal 70 and the size of the first reflected signal 72 received back at the transmitter/receiver probe 14, the amount of attenuation in the pipe 66 can be calculated.

Also, in the pipe 66 is a defect 74. Defect 74 causes a reflected defect signal 76. By calculating the approximate time between the creation of the transmitted signal 70 in the pipe 66 by transmitter/receiver probe 14 and the time the defect signal 76 is received back at the transmitter/receiver probe 14, the approximate location along the pipe 66 of the defect 74 can be calculated. The size of the defect can also be calculated by comparing the size of the defect signal 76 to the size of the first reflected signal 72, taking into consideration the amount of attenuation that occurs per unit length.

In the signal response calibration 42, the first reflected clamp signal 72 is calibrated by comparing the amplitudes of a signal reflected from a weld or a defect that were obtained with the clamp and without the clamp. Thereafter, using equation 5, the reflection coefficient of defect is calculated and its value is related to give the defect size determination 78. The defect size determination 78 is a linear proportion between the amplitude of the defect signal 76 relative to the first reflected signal 72 from clamp 68 after a suitable correction for wave attenuation. The first reflected signal 72 from clamp 68 can also be used in setting the amplitude threshold for detecting defect signal 76 from defect 74.

The rate of attenuation of a signal for unit length can also be determined as is illustrated in FIG. 3. FIG. 3 may have the same type of controls as illustrated in FIG. 1 (though not shown in FIG. 3). The same numerals will be utilized in FIG. 1 as are used in FIG. 3 where applicable. A pulse signal is generated and delivered to the transmitter/receiver probe 14 through connecting cable 40 and a transmitted signal (represented by arrow 56) moves down the pipe 16. At clamp 58, a first reflected signal (represented by arrow 60) is reflected back toward the transmitter/receiver probe 14.

Clamp 62 is also clamped on pipe 16 a further distance "d" down pipe 16. At clamp 62, a second reflected signal (represented by arrow 64) is reflected back towards transmitter/receiver probe 14. The decrease in magnitude between the first reflected signal 60 and the second reflected signal 64 represents the attenuation over the distance "d" in the pipe 16. Therefore, the rate of attenuation can be determined by the use of two separate reflective clamps 58 and 62 a known distance apart. This rate of attenuation is then used to correct for attenuation effect on the detected signals.

What is claimed is:

1. A method of calibrating long range guided wave signals from a pipe under test consisting of the following steps:

first generating near a test area a first guided wave in said pipe under test by a transmitter probe and guided-wave instrumentation;

first propagating said first guided wave along said pipe under test;

first detecting in said pipe under test by a receiver probe and said guided-wave instrumentation first reflected signals from defects, if any;

placing a first reference reflector on said pipe under test near said test area, but outside a dead zone for guided waves;

generating a second guided wave in said pipe under test by said transmitter probe and said guided-wave instrumentation;

second propagating said second guided wave along said pipe under test;

second detecting in said pipe under test by said receiver probe and said guided-wave instrumentation second reflected signals from said first reference reflector and defect signals from said defects, if any;

correcting for attenuation in said reflected signals and said defect signals; and calculating size of said defects using said first reflected signals and said second reflected signals.

2. The method of calibrating a long range guided wave inspection system of a pipe under test as given in claim 1 wherein said first reference reflector is a clamp.

3. The method of calibrating a long range guided wave inspection system of a pipe under test as given in claim 1 including the additional step of calculating attenuation in said pipe under test by connecting a second reference reflector on said pipe under test a known distance from said first reference reflector, said second reference reflector causing second reflecting of a portion of said guided wave for a second reflected signal, comparing of said first reflected signal with said second reflected signal to determine attenuation per linear distance in said pipe under test.

4. The method of calibrating a long range guided wave inspection system of a pipe under test as given in claim 1 wherein said transmitter and said receiver are the same.

* * * * *